United States Patent [19]

Yoakum et al.

[11] Patent Number: 5,484,403
[45] Date of Patent: Jan. 16, 1996

[54] HYPODERMIC SYRINGE FOR IMPLANTING SOLID OBJECTS

[75] Inventors: Jay F. Yoakum, Norco; Sammy E. Wooldridge, Alta Loma, both of Calif.

[73] Assignee: Avid Marketing, Inc., Norco, Calif.

[21] Appl. No.: 223,117

[22] Filed: Apr. 5, 1994

[51] Int. Cl.[6] ............................ A61M 31/00; A61F 13/20
[52] U.S. Cl. .................... 604/59; 604/60; 604/16
[58] Field of Search ................. 604/11, 15, 16, 604/18, 57, 59–64, 230, 187; 606/108, 109

[56] References Cited

U.S. PATENT DOCUMENTS

| | | | |
|---|---|---|---|
| 747,444 | 12/1903 | La Veine | 604/59 |
| 2,269,963 | 1/1942 | Wappler | 604/62 X |
| 3,823,715 | 7/1974 | Holanek et al. | 604/59 |
| 4,490,139 | 12/1984 | Hoizenga et al. | 604/57 |
| 4,492,576 | 1/1985 | Dragan | 433/90 |
| 4,601,699 | 7/1986 | Crain | 604/64 |
| 4,834,704 | 5/1989 | Reinicke | 604/51 |
| 4,936,827 | 6/1990 | Grimm et al. | 604/60 |
| 5,281,197 | 1/1994 | Arias et al. | 604/57 |
| 5,304,119 | 4/1994 | Balaban et al. | 604/51 |
| 5,385,542 | 1/1995 | Rawlings | 604/14 |
| 5,395,319 | 3/1995 | Hirsch et al. | 604/60 |

FOREIGN PATENT DOCUMENTS

| | | | |
|---|---|---|---|
| 0292936 | 11/1988 | European Pat. Off. | 604/60 |
| 8901281 | 12/1990 | Netherlands | 604/60 |
| 0821087 | 9/1959 | United Kingdom | 604/62 |
| 9215362 | 9/1992 | WIPO | 604/60 |

*Primary Examiner*—John D. Yasko
*Assistant Examiner*—Adam J. Cermak
*Attorney, Agent, or Firm*—Robert E. Malm

[57] ABSTRACT

The hypodermic syringe for implanting objects in the bodies of birds, fish, animals, and humans consists of a barrel, a canula attached to one end of the barrel, and a plunger that can be moved back and forth within the barrel. A user implants an object by placing the object inside the canula, making an incision with the canula, and then pushing on the plunger thereby causing the object to move from the canula through the incision and into the body. The canula is designed to securely hold an implant object in a fixed position within the canula from the moment of insertion into the canula until the moment of implantation. The canula is also provided with a window that permits a user to observe the presence of an object and, in the case of objects that are electronic identification tags, to read the data stored in a tag with electromagnetic readers. The plunger is intended to provide the user with the same "feel" as a conventional fluid-injection-type hypodermic syringe. The plunger is also equipped with a pressure-release mechanism to avoid the undesirable effects of air pressure build-up in the barrel which may occur when the plunger is operated by a user.

13 Claims, 1 Drawing Sheet

HYPODERMIC SYRINGE FOR IMPLANTING SOLID OBJECTS

BACKGROUND OF INVENTION

This invention relates to hypodermic syringes and more particularly to hypodermic syringes for implanting solid objects beneath the skin of fish, birds, animals, and humans.

The art or science of restoring or preserving health has always included the injection or withdrawal of fluids from the bodies of living things. With the development of miniaturized mechanical and electrical devices that serve therapeutic purposes and more prosaic purposes such as tracking and identification, the implantation of solid things within a living body has become a reality. The implantation processes first utilized surgical procedures, but as miniaturization techniques became more and more effective, the surgical approach has given way to the use of devices modeled on the hypodermic syringe for injecting fluids.

The hypodermic syringe has long been used to aspirate or inject fluids for diagnostic or therapeutic purposes. It consists of a barrel which constitutes a fluid reservoir, a canula for insertion into the body, the canula being connected in a leak-proof way to the barrel, and a plunger that slides within the barrel and either pushes the fluid in the barrel through the canula and into the body or pulls fluid from the body into the barrel by means of an induced vacuum in the barrel.

The adaptation of the conventional hypodermic syringe for the implantation of solid objects in living bodies has taken a rather predictable path. The adaptation has focussed on objects that are elongated and usually cylindrical that will slide within a more-or-less conventional canula. A pusher rod that slides within the canula and pushes on the object during the implantation process is attached to the plunger, and the sliding seal between the plunger and the barrel is removed, thereby permitting air trapped in the barrel by the plunger to escape around the plunger.

This design has several deficiencies. First of all, the object to be implanted slides easily within the canula and can easily slide out the open end if the user points the syringe downward prior to making the implantation. Second, the "feel" of the syringe to the user during the implantation process is very different from the feel of the conventional fluid-injecting hypodermic syringe because of the absence of the fluid seal between barrel and plunger.

The present invention is intended to overcome both of these deficiencies.

BRIEF SUMMARY OF INVENTION

The hypodermic syringe for implanting solid objects consists of a barrel, a canula that is attached to one end of the barrel, and a plunger that can be moved back and forth within the barrel. The implant object resides within the canula and is implanted in a living body by the user making an incision with the canula and then pushing on the plunger thereby causing the implant object to leave the canula and enter the body through the incision.

The canula is provided with a means for holding the implant object securely within the canula from the moment of insertion of the object into the canula until the moment of implantation. The canula is also provided with a window for viewing and electromagnetically probing the implant object that permits a user to determine whether the canula contains an implant object and, in the case of electronic identification tags, to read by electromagnetic means the data stored in a tag.

The plunger is equipped with a means that causes the plunger to resist movement within the barrel, thereby giving a user the "feel" of a conventional fluid-injecting hypodermic syringe when using the device. The plunger is also equipped with a means for dissipating excess air pressure within the barrel that may occur when a user operates the plunger.

DESCRIPTION OF THE PREFERRED EMBODIMENT

Figure 1:
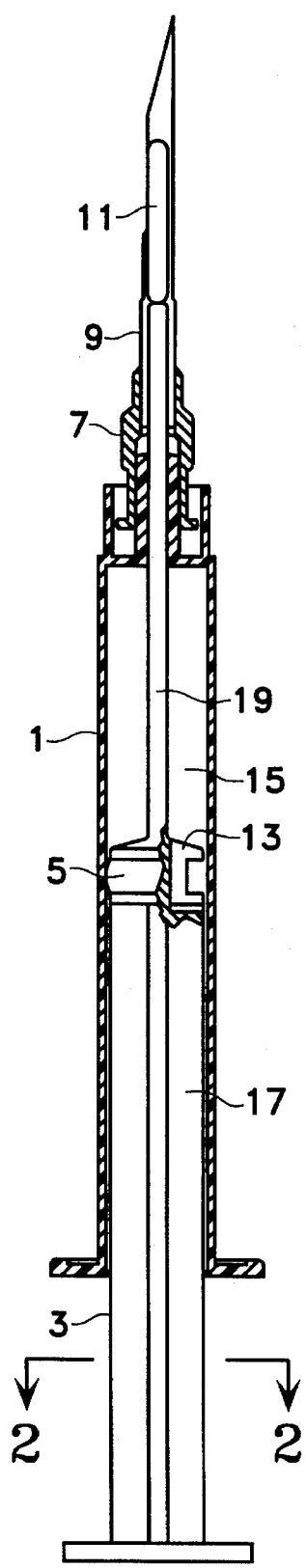
FIG. 1 is a side view of the hypodermic syringe for implanting solid objects shown in partial cross-section.

The preferred embodiment of the invention is shown in FIG. 1 It consists of the barrel 1, the plunger 3, the gasket 5, the hub 7, and the canula 9. A cylindrical object 11 is shown in place in the canula ready to be implanted into a body.

The plastic plunger 3 freely slides within the barrel 1. The presence of the synthetic rubber gasket 5 provides a user with the feel of a conventional fluid-injecting hypodermic syringe. The purpose of the gasket is to provide a frictional force that resists the movement of the plunger, just like the fluid-tight seal in a fluid-injecting syringe. Since there is no need for a leak-proof seal for a solid-object-implanting syringe, the gasket can be made of a porous material or air channels can be incorporated in the gasket to allow air to pass freely through the gasket, thereby avoiding air pressure build-up in the barrel that might force air through the canula and the incision in the body during the implantation procedure.

If the gasket 5 is made of a material that provides a gas-tight seal, the air-escape channel 13 beneath the gasket allows air trapped in region 15 of the barrel 1 to escape to region 17 and the outside environment.

An alternative means for providing a force in opposition to the movement of the plunger 3 into the barrel 1 is a spring interposed between plunger and barrel in region 15 of the barrel. A cylindrical sponge 6 having a hole for the push-rod portion 19 of the plunger to pass through can be substituted for the spring.

The push-rod portion 19 of the plunger 3 freely slides within the canula 9.

The metal hub 7 attaches to the barrel 1 by means of a standard Luerlock connector. The canula 9 is held securely within the hub as a result of crimping the hub.

The implant object 11 is held securely within the stainless-steel canula 9 by crimped regions that exist at four locations spaced at 90-degree intervals around the circumference of the canula.

The barrel 1 is a conventional 3-cm$^3$ plastic hypodermic syringe barrel like those used in fluid-injecting hypodermic syringes and is commercially available from a number of sources.

Figure 2:
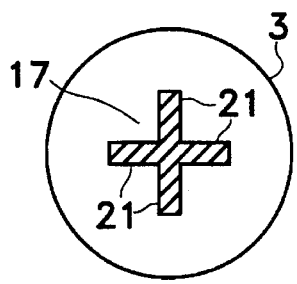
FIG. 2 is a sectional view of that portion of the plunger that resides in the barrel.

An enlarged sectional view of the plunger 3 taken on the plane 2—2 of FIG. 1 is shown in FIG. 2. The four fins 21 in freely-sliding contact with the inside surface of the barrel 1 serve to guide the plunger along a straight-line path. The region 17 of the barrel 1 through which the air trapped in the barrel behind the gasket 5 escapes to the outside environment is shown in the context of the plunger.

Figure 3:
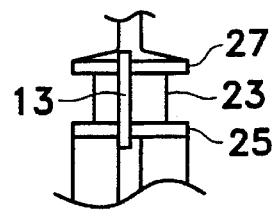
FIG. 3 is a side view orthogonal to the side view of FIG. 1 showing the portion of the plunger containing the gasket recess.

An enlarged side view of the portion of the plunger containing the gasket channel 23 but without the gasket 5 is shown in FIG. 3. The air-escape channel 13 is shown extending through the walls 25 and 27 of the gasket channel 23.

Figure 4A:
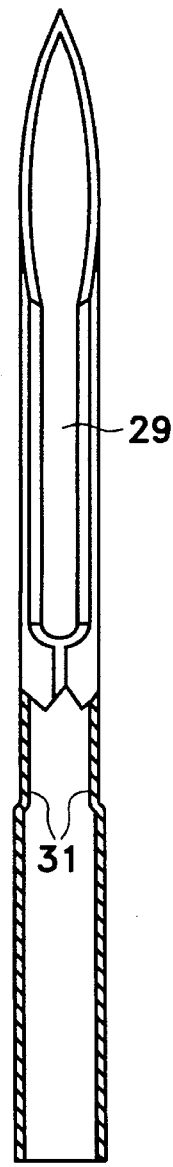
FIG. 4 shows two orthogonal views of the canula.
Figure 4B:
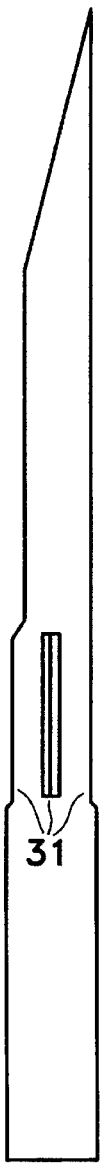

Two orthogonal views of the canula 9 are shown in FIG. 4. The canula is designed to handle cylindrical implant objects having outside diameters falling within a range defined by a minimum outside diameter (minOD) and a maximum outside diameter (maxOD). The minimum inside diameter (minID) that a canula is permitted to have is made just enough larger than the maxOD as to allow an implant object having a maxOD outside diameter to move back and forth without binding in a canula having a minID inside diameter.

The point of the canula is formed by a 12-degree bevel.

The slot 29 has a length approximately equal to two-thirds of the nominal length of the implant object. The width of the slot is equal to no more than one-half and no less than one-third the nominal diameter of the implant object. The purpose of the slot is for the user to be able to see if an implant object is present in the canula, and, in the case of an identification tag, to be able to read either electronically or visually, depending upon the nature of the tag, the data contained on or within the tag.

The four crimp regions 31 (the one on the underside does not show) extend from the closed end of the slot 29 for a distance equal to about one-quarter of the nominal diameter of the implant object. The crimp regions taper inward so that the distance between opposing crimp regions is greater than the maxOD of the implant object at the slot end and is less than the minOD at the terminal ends of the crimp regions. With this dimensional arrangement, any implant object satisfying the minOD and maxOD requirements can be pushed into the canula and be held securely by the crimp regions at some position within the crimp regions.

An alternative embodiment of the canula omits the crimp regions 31 and utilizes the existence of the slot 29 as a means for holding the implant object in the canula. The maxID of the canula is chosen to be slightly less than the minOD of the implant object. Then, as an implant object satisfying the minOD and maxOD requirements is pushed into the open end of the canula, the edges of the slot spring apart and hold the implant object in the canula until it is implanted int a body.

What is claimed is:

1. A device for implanting solid objects comprising:

a canula adapted to receive an implant object into its interior at the distal end and having an obstruction which prevents the implant object from moving from the distal end to the proximal end;

a means for holding the implant object in a fixed position within the canula prior to implantation, the holding means being selected from the group conisting of (1) an open-ended slot at the distal end of the canula, the inside diameter of the canula being less than the outside diameter of the implant object and (2) a plurality of crimped regions on the canula surface.

2. A device for implanting solid objects comprising:

a canula adapted to receive an implant object into its interior at the distal end and having an obstruction which prevents the implant object from moving from the distal end to the proximal end;

a means for holding the implant object in a fixed position within the canula prior to implantation;

an access means for viewing and electromagnetically probing the implant object when it is lodged within the canula.

3. The device of claim 2 wherein the access means is a slot in the canula.

4. The device of claim 2 further comprising:

a barrel attached to the canula;

a plunger dimensioned to enter the barrel and the canula, the movement of the plunger within the barrel and the canula causing the object lodged within the canula to be ejected.

5. A device for implanting solid objects comprising:

a canula adapted to receive an implant object into its interior at the distal end and having an obstruction which prevents the implant object from moving from the distal end to the proximal end;

a means for holding the implant object in a fixed position within the canula prior to implantation;

a barrel attached to the canula;

a plunger dimensioned to enter the barrel and the canula, the movement of the plunger within the barrel and the canula causing the object when lodged within the canula to be ejected, the plunger comprising a means for guiding the plunger as it moves within the barrel, a means for applying a force to the plunger to resist movement of the plunger within the barrel, and a means for avoiding the build-up of air pressure in the barrel that would oppose the movement of the plunger.

6. The device of claim 5 wherein (1) the guiding means is a portion of the plunger that makes sliding contact with the inside surface of the barrel and the force-applying means is a gasket in intimate contact with the guiding-means portion of the plunger and making contact with the inside surface of the barrel thereby providing for a frictional force resisting the movement of the plunger as the plunger moves within the barrel, the gasket dividing the barrel into two regions, and (2) the means for avoiding the build-up of air pressure in the barrel is an air passage connecting the two regions of the barrel.

7. A device for implanting solid objects comprising:

a canula adapted to receive an implant object into its interior at the distal end and having an obstruction which prevents the implant object from moving from the distal end to the proximal end;

a means for holding the implant object in a fixed position within the canula prior to implantation;

an access means for viewing and electromagnetically probing the implant object when it is lodged within the canula;

a barrel attached to the canula;

a plunger dimensioned to enter the barrel and the canula, the movement of the plunger within the barrel and the canula causing the object when lodged within the canula to be ejected, the plunger comprising a means for guiding the plunger as it moves within the barrel, a means for causing the implant object to move out of the canula as the plunger moves within the barrel, a means for applying a force to the plunger to resist movement of the plunger within the barrel, and a means for avoiding the build-up of air pressure in the barrel that would oppose the movement of the plunger.

8. The device of claim 7 wherein (1) the guiding means is a portion of the plunger that makes sliding contact with the inside surface of the barrel and the force-applying means is a gasket in intimate contact with the guiding means portion of the plunger and making contact with the inside surface of the barrel thereby providing for a frictional force resisting the movement of the plunger as the plunger moves within the barrel, the gasket dividing the barrel into two regions, and (2) the means for avoiding the build-up of air pressure in the barrel is an air passage connecting the two regions of the barrel.

9. A device for implanting solid objects comprising:

a canula dimensioned to receive an implant object into its interior;

a means for holding the implant object in a fixed position within the canula prior to implantation;

an access means for viewing and electromagnetically probing the implant object when it is lodged within the canula.

a barrel attached to the canula;

a plunger that moves within the barrel and the canula, the plunger comprising a means for applying a force to the plunger to resist movement of the plunger within the barrel and a means for avoiding the build-up of air pressure in the barrel that would oppose the movement of the plunger, the force-applying means being a gasket in intimate contact with a portion of the plunger and making contact with the inside surface of the barrel thereby providing for a frictional force resisting the movement of the plunger as the plunger moves within the barrel, the gasket dividing the barrel into two regions, the means for avoiding the build-up of air pressure in the barrel being an air passage connecting the two regions of the barrel.

10. A plunger for use with a barrel and a canula attached thereto for implanting solid objects, the plunger when sliding within the barrel and the canula implanting an implant object that is lodged within the canula, the plunger comprising:

a means for applying a force to the plunger to resist movement of the plunger within the barrel, the means being selected from the group consisting of (1) a device in contact with a portion of the exterior surface of the plunger and the interior surface of the barrel and (2) a compressible device;

a means for avoiding the build-up of air pressure in the barrel that would oppose the movement of the plunger.

11. A plunger for use with a barrel and a canula attached thereto for implanting solid objects, the plunger when sliding within the barrel and the canula implanting an implant object that is lodged within the canula, the plunger comprising:

a means for applying a force to the plunger to resist movement of the plunger within the barrel, the force-applying means being a gasket in intimate contact with a portion of the plunger and making contact with the inside surface of the barrel thereby providing for a frictional force resisting the movement of the plunger as the plunger moves within the barrel, the gasket dividing the barrel into two regions;

a means for avoiding the build-up of air pressure in the barrel that would oppose the movement of the plunger, the means for avoiding the build-up of air pressure in the barrel being an air passage connecting the two regions of the barrel.

12. A device for implanting solid objects comprising:

a barrel;

a canula dimensioned to receive the implant object into its interior, the canula being attached to the barrel;

a plunger that slides within the barrel and the canula and implants the implant object when the implant object is lodged within the canula, the plunger comprising:

a means for applying a force to the plunger to resist movement of the plunger within the barrel, the means being selected from the group consisting of (1) a device in contact with a portion of the exterior surface of the plunger and the interior surface of the barrel and (2) a compressible device;

a means for avoiding the build-up of air pressure in the barrel that would oppose the movement of the plunger.

13. A device for implanting solid objects comprising:

a barrel;

a canula dimensioned to receive the implant object into its interior, the canula being attached to the barrel;

a plunger that slides within the barrel and the canula, the plunger comprising:

a means for applying a force to the plunger to resist movement of the plunger within the barrel, the force-applying means being a gasket in intimate contact with a portion of the plunger and making contact with the inside surface of the barrel thereby providing for a frictional force resisting the movement of the plunger as the plunger moves within the barrel, the gasket dividing the barrel into two regions;

a means for avoiding the build-up of air pressure in the barrel that would oppose the movement of the plunger, the means for avoiding the build-up of air pressure in the barrel being an air passage connecting the two regions of the barrel.

* * * * *